(12) United States Patent
Cincotta

(10) Patent No.: US 10,688,155 B2
(45) Date of Patent: *Jun. 23, 2020

(54) COMBINATION OF DOPAMINE AGONISTS PLUS FIRST PHASE INSULIN SECRETAGOGUES FOR THE TREATMENT OF METABOLIC DISORDERS

(71) Applicant: VeroScience LLC, Tiverton, RI (US)

(72) Inventor: Anthony H. Cincotta, Tiverton, RI (US)

(73) Assignee: VeroScience LLC, Tiverton, RI (US)

( * ) Notice: Subject to any disclaimer, the term of this patent is extended or adjusted under 35 U.S.C. 154(b) by 71 days.

This patent is subject to a terminal disclaimer.

(21) Appl. No.: 15/874,430

(22) Filed: Jan. 18, 2018

(65) Prior Publication Data

US 2018/0140675 A1    May 24, 2018

Related U.S. Application Data

(63) Continuation of application No. 15/165,485, filed on May 26, 2016, now Pat. No. 9,895,422, which is a continuation of application No. 14/506,353, filed on Oct. 3, 2014, now Pat. No. 9,352,025, which is a continuation of application No. 13/375,810, filed as application No. PCT/US2010/037605 on Jun. 7, 2010, now Pat. No. 8,877,708.

(60) Provisional application No. 61/217,906, filed on Jun. 5, 2009.

(51) Int. Cl.
| | |
|---|---|
| *A61K 38/28* | (2006.01) |
| *A61K 38/22* | (2006.01) |
| *A61K 31/4985* | (2006.01) |
| *A61K 38/26* | (2006.01) |
| *A61K 31/166* | (2006.01) |
| *A61K 31/198* | (2006.01) |
| *A61K 31/4453* | (2006.01) |
| *A61K 31/48* | (2006.01) |

(52) U.S. Cl.
CPC ............ *A61K 38/22* (2013.01); *A61K 31/166* (2013.01); *A61K 31/198* (2013.01); *A61K 31/4453* (2013.01); *A61K 31/48* (2013.01); *A61K 31/4985* (2013.01); *A61K 38/26* (2013.01); *A61K 38/28* (2013.01)

(58) Field of Classification Search
CPC ................................. A61K 38/26; A61K 38/22
See application file for complete search history.

(56) References Cited

U.S. PATENT DOCUMENTS

| | | |
|---|---|---|
| 4,009,265 A | 2/1977 | Howard |
| 4,338,304 A | 7/1982 | Kimimae et al. |
| 4,446,138 A | 5/1984 | Pack |
| 4,659,715 A | 4/1987 | Meier et al. |
| 4,749,709 A | 6/1988 | Meier et al. |
| 4,783,369 A | 11/1988 | Sugata et al. |
| 4,783,469 A | 11/1988 | Meier et al. |
| 4,791,125 A | 12/1988 | Clark |
| 4,971,969 A | 11/1990 | Carlier et al. |
| 5,006,526 A | 4/1991 | Meier et al. |
| 5,066,495 A | 11/1991 | Moro et al. |
| 5,344,832 A | 9/1994 | Cincotta et al. |
| 5,468,755 A | 11/1995 | Cincotta et al. |
| 5,496,803 A | 3/1996 | Meier et al. |
| 5,554,623 A | 9/1996 | Cincotta et al. |
| 5,565,454 A | 10/1996 | Cincotta |
| 5,585,347 A | 12/1996 | Meier et al. |
| 5,614,492 A | 3/1997 | Habener |
| 5,626,860 A | 5/1997 | Cincotta et al. |
| 5,635,512 A | 6/1997 | Cincotta et al. |
| 5,654,313 A | 8/1997 | Cincotta et al. |
| 5,668,155 A | 9/1997 | Cincotta et al. |
| 5,679,685 A | 10/1997 | Cincotta et al. |
| 5,688,794 A | 11/1997 | Meier et al. |
| 5,696,128 A | 12/1997 | Cincotta et al. |
| 5,700,795 A | 12/1997 | Cincotta et al. |
| 5,700,800 A | 12/1997 | Cincotta et al. |
| 5,712,265 A | 1/1998 | Cincotta et al. |
| 5,714,519 A | 2/1998 | Cincotta et al. |
| 5,716,932 A | 2/1998 | Meier et al. |
| 5,716,933 A | 2/1998 | Meier et al. |
| 5,716,957 A | 2/1998 | Cincotta et al. |
| 5,716,962 A | 2/1998 | Cincotta et al. |
| 5,719,160 A | 2/1998 | Cincotta et al. |
| 5,731,287 A | 3/1998 | Meier et al. |
| 5,731,312 A | 3/1998 | Cincotta et al. |
| 5,741,503 A | 4/1998 | Cincotta et al. |
| 5,744,477 A | 4/1998 | Cincotta et al. |

(Continued)

FOREIGN PATENT DOCUMENTS

| | | |
|---|---|---|
| CN | 1678313 | 10/2005 |
| CN | 1950078 | 4/2007 |

(Continued)

OTHER PUBLICATIONS

Extended European Search Report in Application No. 18169183.3, dated Aug. 22, 2018, 11 pages.

(Continued)

*Primary Examiner* — Gyan Chandra
(74) *Attorney, Agent, or Firm* — Fish & Richardson P.C.

(57) ABSTRACT

The present invention is directed to a method of treating a metabolic disorder or key elements of a metabolic disorder such method comprising the use of an agent(s) that increases central dopaminergic activity plus a first-phase insulin secretagouge.

57 Claims, No Drawings

(56) References Cited

U.S. PATENT DOCUMENTS

| | | |
|---|---|---|
| 5,750,519 A | 5/1998 | Cincotta et al. |
| 5,756,513 A | 5/1998 | Cincotta et al. |
| 5,760,047 A | 6/1998 | Cincotta et al. |
| 5,792,748 A | 8/1998 | Cincotta et al. |
| 5,830,895 A | 11/1998 | Cincotta et al. |
| 5,854,255 A | 12/1998 | Cincotta et al. |
| 5,866,584 A | 2/1999 | Cincotta et al. |
| 5,872,127 A | 2/1999 | Cincotta et al. |
| 5,872,133 A | 2/1999 | Cincotta et al. |
| 5,877,183 A | 3/1999 | Cincotta |
| 5,902,811 A | 5/1999 | Cincotta |
| 5,905,083 A | 5/1999 | Cincotta et al. |
| 6,004,972 A | 12/1999 | Cincotta et al. |
| 6,011,049 A | 1/2000 | Whitcomb |
| 6,040,292 A | 3/2000 | Sommer |
| 6,071,914 A | 6/2000 | Cincotta et al. |
| 6,075,020 A | 6/2000 | Cincotta et al. |
| 6,166,017 A | 12/2000 | Marin |
| 6,197,765 B1 | 3/2001 | Vardi et al. |
| 6,248,375 B1 | 6/2001 | Gilles et al. |
| 6,277,887 B1 | 8/2001 | Young |
| 6,322,976 B1 | 11/2001 | Aitman et al. |
| 6,365,176 B1 | 4/2002 | Bell et al. |
| 6,376,464 B1 | 4/2002 | Dasseux et al. |
| 6,410,339 B1 | 6/2002 | Marin |
| 6,441,036 B1 | 8/2002 | Berge |
| 6,506,799 B1 | 1/2003 | Dasseux |
| 6,855,707 B2 | 2/2005 | Cincotta |
| 7,223,728 B2 | 5/2007 | Yakubu-Madus et al. |
| 7,258,871 B2 | 8/2007 | Horowski et al. |
| 7,572,789 B2 | 8/2009 | Cowen et al. |
| 7,888,310 B2 | 2/2011 | Cincotta |
| 8,021,681 B2 | 9/2011 | Cincotta |
| 8,137,992 B2 | 3/2012 | Cincotta |
| 8,137,993 B2 | 3/2012 | Cincotta |
| 8,137,994 B2 | 3/2012 | Cincotta |
| 8,431,155 B1 | 4/2013 | Cincotta et al. |
| 8,613,947 B2 | 12/2013 | Cincotta et al. |
| 8,741,918 B2 | 6/2014 | Cincotta |
| 8,821,915 B2 | 9/2014 | Cincotta |
| 8,877,708 B2 | 11/2014 | Cincotta |
| 9,192,576 B2 | 11/2015 | Cincotta et al. |
| 9,205,084 B2 | 12/2015 | Cincotta |
| 9,352,025 B2 | 5/2016 | Cincotta |
| 2001/0002269 A1 | 5/2001 | Zhao |
| 2001/0016582 A1 | 8/2001 | Cincotta et al. |
| 2002/0187985 A1 | 12/2002 | Cincotta |
| 2003/0087963 A1 | 5/2003 | Senanayake et al. |
| 2003/0212085 A1 | 11/2003 | McCall et al. |
| 2004/0028613 A1 | 2/2004 | Quay |
| 2004/0077679 A1 | 4/2004 | Cincotta |
| 2004/0081678 A1 | 4/2004 | Cincotta |
| 2004/0180088 A1 | 9/2004 | Dudhara et al. |
| 2004/0214887 A1 | 10/2004 | Dasseux et al. |
| 2004/0220190 A1 | 11/2004 | Cincotta |
| 2005/0054652 A1 | 3/2005 | Cincotta |
| 2005/0054734 A1 | 3/2005 | Cincotta |
| 2005/0215558 A1 | 9/2005 | Cincotta |
| 2005/0220855 A1 | 10/2005 | Horowski et al. |
| 2005/0232989 A1 | 10/2005 | Piene et al. |
| 2005/0245612 A1 | 11/2005 | Blass |
| 2006/0057207 A1 | 3/2006 | Ziegler et al. |
| 2006/0111348 A1 | 5/2006 | Kampen et al. |
| 2006/0239928 A1 | 10/2006 | Heit et al. |
| 2007/0129312 A1 | 6/2007 | Yatvin et al. |
| 2007/0191371 A1 | 8/2007 | Bennett et al. |
| 2007/0225379 A1 | 9/2007 | Carrara et al. |
| 2007/0292479 A1 | 12/2007 | Podhaisky et al. |
| 2008/0200453 A1 | 8/2008 | Cincotta |
| 2008/0293735 A1 | 11/2008 | Cincotta |
| 2009/0054512 A1* | 2/2009 | Foley ............ A61K 31/155 514/423 |
| 2009/0137598 A1 | 5/2009 | Cincotta |
| 2009/0143390 A1 | 6/2009 | Cincotta |
| 2009/0305225 A1 | 12/2009 | Galbraith |
| 2010/0035886 A1 | 2/2010 | Cincotta et al. |
| 2012/0148499 A1 | 6/2012 | Tsien |
| 2012/0283193 A1 | 11/2012 | Spitzer |
| 2013/0197005 A1 | 8/2013 | Cincotta |
| 2013/0274246 A1 | 10/2013 | Cincotta |
| 2014/0051685 A1 | 2/2014 | Cincotta |
| 2014/0249136 A1 | 9/2014 | Cincotta |
| 2014/0342975 A1 | 11/2014 | Cincotta |
| 2015/0011554 A1 | 1/2015 | Cincotta et al. |
| 2015/0335641 A1 | 11/2015 | Cincotta |
| 2016/0038424 A1 | 2/2016 | Cincotta et al. |
| 2016/0263181 A1 | 9/2016 | Cincotta |
| 2016/0271222 A1 | 9/2016 | Cincotta |

FOREIGN PATENT DOCUMENTS

| | | |
|---|---|---|
| EP | 1004594 | 5/2000 |
| JP | 1997-301892 | 11/1997 |
| JP | 2002-539163 | 11/2002 |
| JP | 2005-533768 | 11/2005 |
| JP | 2007-502823 | 2/2007 |
| JP | 2010-157037 | 2/2010 |
| KR | 20100091944 | 8/2010 |
| RU | 2467743 | 11/2012 |
| WO | WO1993012701 | 7/1993 |
| WO | WO1993012793 | 7/1993 |
| WO | WO1994015211 | 7/1994 |
| WO | WO1995017170 | 6/1995 |
| WO | WO1995018614 | 7/1995 |
| WO | WO1996000396 | 1/1996 |
| WO | WO1996013251 | 5/1996 |
| WO | WO1996039050 | 12/1996 |
| WO | WO1996039052 | 12/1996 |
| WO | WO1996039868 | 12/1996 |
| WO | WO1997006786 | 2/1997 |
| WO | WO1997041873 | 11/1997 |
| WO | WO1998008871 | 3/1998 |
| WO | WO1998031368 | 7/1998 |
| WO | WO2000032171 | 6/2000 |
| WO | WO2000054774 | 9/2000 |
| WO | WO2004010946 | 2/2004 |
| WO | WO2005016321 | 2/2005 |
| WO | WO2005049088 | 6/2005 |
| WO | WO2005120492 | 12/2005 |
| WO | WO2006103417 | 10/2006 |
| WO | WO2006128022 | 11/2006 |
| WO | WO2007002518 | 1/2007 |
| WO | WO2007085498 | 8/2007 |
| WO | WO2007140191 | 12/2007 |
| WO | WO2009091576 | 7/2009 |

OTHER PUBLICATIONS

"Alternative routes of drug administration—advantages and disadvantages (subject review). American Academy of Pediatrics. Committee on Drugs," *Pediatrics*, 100(1):143-152, Jul. 1997.

Aellig et al., "Comparative pharmacokinetic investigations with tritium-labeled ergot alkaloids after oral and intravenous administration man," *Int J Clin Pharmacol Biopharm.*, 15(3):106-112, Mar. 1997.

Alford et al., "The effects of variations in carbohydrate, protein, and fat content of the diet upon weight loss, blood values, and nutrient intake of adult obese women," *J Am Diet Assoc.*, 90(4):534-540, Apr. 1990.

Ansel et al., Pharmaceutical Dosage Forms and Drug Delivery Systems, 1995, 78-81.

Armentero et al., "Dopamine Receptor Agonists Media europrotection in malonate-Induced striatal lesion in the Rat," *Experimental Neurology*, Dec. 2002, 178(2):301-305.

Arteriosclerosis/atherosclerosis Definition-Diseases and Condition, by Mayo Clinic staff, May 2014, accessed on Oct. 8, 2014; available at http://www.mayoclinic.org/diseases-conditions/arteriosclerosis-atherosclerosis/basics/definition/con-20026972, 9 pages.

Baba et al., "High protein vs high carbohydrate hypoenergetic diet for the treatment of obese hyperinsulinemic subjects," *Int J Obes Relat Metab Disord.*, 23(11):1202-1206, Nov. 1999.

(56) References Cited

OTHER PUBLICATIONS

Bénés et al., "Transmucosal, oral controlled-release, and transdermal drug administration in human subjects: a crossover study with melatonin," J Pharm Sci., 86(10):1115-1119, Oct. 1997.
Breen et al., "Insulin increases reendothelialization and inhibits cell migration and neointimal growth after arterial injury," Arterioscler Thromb Vase Biol. 2009, 29:1060-1066.
Bruemmer et al., "Thiazolidinedione regulation of smooth muscle cell proliferation," The American Journal of Medicine, Dec. 8, 2003, 115(BA):87S-92S.
Carranza et al., "L-Dopa uptake and dopamine production in proximal tubular cells are regulated by beta(2)-adrenergic receptors," Am J Physiol Renal Physiol., 279(1):F77-F83, Jul. 2000.
Cavero et al., "Heart rate lowering effects of N, N-di-n-Propyldopamine in rats: evidence for stimulation of central dopamine receptors leading to inhibition of sympathetic tone and enhancement of parasympathetic outflow," Journal of Pharmacology and Experimental Therapeutics, 1981, 219(2):510-519.
Ciccarelli et al., "Double blind randomized study using oral or injectable bromocriptine in patients with hyperprolactinaemia," Clin Endocrinol (Oxf)., 40(2):193-198, Feb. 1994.
Cicinelli et al., "Nasal spray administration of bromocriptine: pharmacology and effect on serum prolactin level in puerperal women," Gynecol Endocrinol., 10(6):391-396, Dec. 1996.
Cicinelli et al., "Nasal spray bromocriptine: effects on serum prolactin in puerperal women," Acta Obstet Gynecol Scand., 75(8):730-733, Sep. 1996.
Cicinelli et al., "Nasal spray vs oral administration of bromocriptine: pharmacology and effect on serum prolactin in puerperal women," J Endocrinol Invest., 19(7):427-432, Jul.-Aug. 1996.
Cincotta et al., "Bromocriptine improves glycaemic control and serum lipid profile in obese Type 2 diabetic subjects: a new approach in the treatment of diabetes," Expert Opin Investig Drugs., 8(10):1683-1707, Oct. 1999.
Dai et al., "LOX-1, a bridge between GLP-1 and mitochondrial ROS generation in human vascular smooth muscle cells," Biochemical and Biophysical Research Communications, 2013, 437:62-66.
Degim et al., "Transdermal administration of bromocriptine," Biol Pharm Bull., 26(4):501-505, Apr. 2003.
Dios et al., "Troglitazone, but not rosiglitazone, inhibits na/h exchange activity and proliferation of macrovascular endothelial cells," Journal of Diabetes and its Complications, 2001, 15:120-127.
Dormandy et al., "Secondary prevention of macrovascular events in patients with type 2 diabetes in the PROactive Study (PROspective pioglitazone Clinical Trial in macrovascular events): a randomised controlled trial," Lancet, Oct. 8, 2005, 366:1279-89.
Dubey et al., "Pioglitazone attenuates hypertension and inhibits growth of renal arteriolar smooth muscle in rats," American Physiological Society, 1993, R726-R732.
Duckworth et al., "Glucose control and vascular complications in veterans with type 2 diabetes," The New England Journal of Medicine, Jan. 8, 2009, 360:129-139.
Durant et al., "Bromocriptine-induced hyperglycemia in nonobese diabetic mice: kinetics and mechanisms of action," Rev Diabet Stud., 4(3):185-194, Epub Nov. 2007.
Durif et al., "Efficacy of sublingual apomorphine in Parkinson's disease," J Neurol Neurosurg Psychiatry., 53(12):1105, Dec. 1990.
English translation of Chinese article entitled: Compatibility of dopamine hydrochloride and inosine in transfusion: Journal of Medical Science Yanbian University, vol. 21, No. 2, p. 102, Feb. 21, 1998 (Feb. 21, 1998).
Ervinna et al., "Anagliptin, a dpp-4 inhibitor, suppresses proliferation of vascular smooth muscles and monocyte inflammatory reaction and attenuates atherosclerosis in male apo e-deficient mice," Endocrinology, Mar. 2013, 145(3):1260-1270.
Fluckiger, E., Editorial Note, 1992, Experiential, 48:248.
Freedman, Marjorie R., King, Janet, and Kennedy, Eileen, "Popular Diets: A Scientific view", Obesity Research, vol. 9, Supp. 1, pp. IS•40S (Mar. 2001).

Fukuda et al., "Troglitazone inhibits growth and improves insulin signaling by suppression of angiotensin ii action in vascular smooth muscle cells from spontaneously hypertensive rats," Atherosclerosis, 2002, 163:229-239.
Gadde et al., "Bupropion for weight loss: an investigation of efficacy and tolerability in overweight and obese women," Obesity Research, Sep. 2001, 9(9):544-551.
Garcia-Robles et al., "Dopamine control of aldosterone secretion in end-stage renal failure," Rev Esp Fisiol, 42(2):257-263, Jun. 1986.
Gaziano et al., "Effect of bromocriptine-qr (a quick-release formulation of bromocriptine mesylate) on major adverse cardiovascular events in type 2 diabetes subjects," J Am Heart Assoc, 2012, 1:doi:10.1161/JAHA.112.002279, 11 pages.
Gaziano et al., "Randomized clinical trial of quick-release bromocriptine among patients with type 2 diabetes on overall safety and cardiovascular outcomes," Diabetes Care, Jul. 2010, 33:1503-1508 (12 total pages).
Gerstein et al., "Effects of intensive glucose lowering in type 2 diabetes," The New England Journal of Medicine, Jun. 12, 2008, 358:2545-59.
Gerstein, "Basal insulin and cardiovascular and other outcomes in dysglycemia," The New England Journal of Medicine, Jul. 26, 2012, 367:319-328.
Goto et al., "Exendin-4, a glucagon-like peptide-1 receptor agonist, reduces intimal thickening after vascular injury," Biochemical and Biophysical Research Communications, 2011, 405:79-84.
Gouni-Berthold et al., "Troglitazone and rosiglitazone inhibit the low density lipoprotein-induced vascular smooth muscle cell growth," Exp Clin Endocrinol Diabetes, 2001, 109:203-209.
Grundy, "Drug therapy of the metabolic syndrome. minimizing the emerging crisis in polypharmacy," Nature Reviews/Drug Discovery, vol. 5, Apr. 2006, pp. 295-309.
Ha et al., "High glucose induces connective tissue growth factor expression and extracellular matrix accumulation in rat aorta vascular smooth muscle cells via extracellular signal-regulated kinase 1 / 2," Korean J Physiol Pharmacol, Aug. 2013, 17:307-314.
Haase et al., "Control of prolactin-secreting macroadenomas with parenteral long-acting bromocriptine in 30 patients treated for up to 3 years," Clin Endocrinol (Oxf)., 38(2):165-176, Feb. 1993.
Hara et al., "Central dopaminergic function in stroke prone spontaneously hypertensive rats effects of chronic treatment with lisuride on the impaired swimming ability," Database Accession No. PREV198376013141 and Folia Pharmacologica Japonica, 1982, 80(5):395-394 (Abstract only—2 pages).
Hasko et al., "Modulation of lipopolysaccharide-induced tumor necrosis factor-α and nitric oxide production by dopamine receptor agonists and antagonists in mice," Immunology Letters, 1996, 49(3):143-147.
Hisahara et al., "Review Article Dopamine Receptors and Parkinson's Disease," International Journal of Medicinal Chemistry, 2011, 16 pages.
Home et al., "Rosiglitazone evaluated for cardiovascular outcomes in oral agent combination therapy for type 2 diabetes (record): a multicentre, randomised, open-label trial," Lancet, Jun. 20, 2009, 373:2125-35.
Hsueh et al., "Insulin signaling in the arterial wall," Am J Cardiol, 1999, 84:21J-24J.
Humbert et al., "Human pharmacokinetics of dihydroergotamine administered by nasal spray," Clin Pharmacol Ther., 60(3):265-275, Sep. 1996.
Jaspers et al., "Long-term treatment of acromegalic patients with repeatable parenteral depot-bromocriptine," Clin Investig., 71(7):547-551, Jul. 1993.
Kalra et al., "Dopamine: the forgotten felon in type 2 diabetes," Recent Pat Endocr Metab Immune Drug Discov., 5(1):61-65, Jan. 2011.
Katz et al., "Successful treatment of a prolactin-producing pituitary macroadenoma with intravaginal bromocriptine mesylate: a novel approach to intolerance of oral therapy," Obstet Gynecol., 73(3 Pt 2):517-520, Mar. 1989.
Kharkevich, DA, Pharmacology (textbook), Moscow, GAOTAR-Media (2006), pp. 39 and 44.

(56) References Cited

OTHER PUBLICATIONS

Kihara et al., "Protective effect of dopamine D2 agonists in cortical neurons via the phosphatidylinositol 3 kinase cascade," *J Neurosci Res.*, 70(3):274-282, Nov. 1, 2002.
Kok et al., "Activation of dopamine D2 receptors simultaneously ameliorates various metabolic features of obese women," American Journal of Physiology-Endocrinology and Metabolism, vol. 291, Jun. 27, 2006, pp. E1038-E1043.
Kuo et al., "Hypothalamic neuropeptide Y (NPY) and the attenuation of hyperphagia in streptozotocin diabetic rats treated with dopamine D1/D2 agonists," British Journal of Pharmacology, 2006, 148:640-647.
Lam, Carol K. L. et al., Activation of N-Methyl-D-aspartate (NMDA) Receptors in the Dorsal Vagal Complex Lowers Glucose Production, J Biol Chem, vol. 285, No. 29, pp. 21913-21921, Jul. 16, 2010.
Lan et al., "Vascular fibrosis in atherosclerosis," Cardiovascular Pathology, 2013, 22:4101-407.
Li et al., "GLP-1 receptor stimulation preserves primary cortical and dopaminergic neurons in cellular and and rodent models of stroke and parkinsonism," *Proc Natl Acad Sci U S A.*, 106(4):1285-1290, Epub Jan. 21, 2009.
Lightell et al., "Loss of canonical insulin signaling accelerates vascular smooth muscle cell proliferation and migration through changes in p27kip1 regulation," Endocrinology, Feb. 2011, 152(2):651-658.
Lusis, "Atherosclerosis," *Nature*, 407(6801): 233-241, Sep. 14, 2000 [author manuscript].
Mannelli et al., "Effects of different dopaminergic antagonists on bromocriptine-induced inhibition of norepinephrine release," Journal of Clinical Endocrinology and Metabolism, 1984, 59(1):74-78.
Mattox et al., "Dopamine agonists for reducing depression associated with hyperprolactinemia," *J Reprod Med.*, 31(8):694-698, Aug. 1986.
Meier et al., "Timed bromocriptine administration reduces body fat stores in obese subjects and hyperglycemia in type II diabetics," Experientia, 1992, 48(3):248-253.
Narkar et al., "Dopamine D2-like receptor agonist bromocriptine protects against ischemia/reperfusion injury in rat kidney," Kidney Int., 66(2):633-640, Aug. 2004.
NCBI Reference Sequence XP-002587257, Hypothetical Protein BRAFLDRAFT-61678 (Branchiostoma floridae), Accession No. XP_002587257, GI No. 260784404, dated Oct. 8, 2009, (retrieved from the Internet: Feb. 23, 2015), 2 pages.
Nielsen et al., "Desipramine and some other antidepressant drugs decrease the major norepinephrine metabolite 3,4-dihydroxyphenylglycol-sulphate in the rat Brain," Naunyn Schmiedebergs Arch Pharmacol., 300(1):93-99, Oct. 1977.
NIH Publication No. 05-4642 [online], www.diabetes.niddk.nih.gov, Jan. 2005 [retrieved on Nov. 6, 20086]. Retrieved from the Internet: <URL: http://diabetes.niddk.nih.gov/dm/pubs/diagnosis/>.
Nordin et al., "Bromocriptine treatment of depressive disorders," *Acta Psychiatrica Scandinavica*, 64(1):25-33, 1981.
O'Neill et al., "Dopamine D2 receptor agonists protect against ischaemia induced hippocampal neurodegeneration in global cerebral ischaemia," European Journal of Pharmacology, Jul. 3, 1998, 352(1):37-46.
Ondo et al., "A novel sublingual apomorphine treatment for patients with fluctuating Parkinson's disease," *Mov Disord.*, 14(4):664-668, Jul. 1999.
Park et al., "The inhibition of insulin-stimulated proliferation of vascular smooth muscle cells by rosiglitazone is mediated by the akt-mtor-p70s6k pathway," Yonsei Med J, 2008, 49(4):592-600.
Patel et al., "Intensive blood glucose control and vascular outcomes in patients with type 2 diabetes," The New England Journal of Medicine, Jun. 6, 2008, 358:2560-72.
Peces et al., "Prolactin in chronic renal failure, haemodialysis, and transplant patients," Proc Eur Dial Transplant Assoc., 16:700-702, 1979.

Piacentini et al., "Effect of bupropion on hippocampal neurotransmitters and on peripheral hormonal concentrations in the rat," Journal of Applied Physiology, vol. 95, 2003, pp. 652-656.
Pietz et al., "Subcutaneous apomorphine in late stage Parkinson's disease: a long term follow up," *J Neurol Neurosurg Psychiatry*, 65(5):709-716, Nov. 1998.
Pijl and Meinders, "Modulation of monoaminergic neural circuits: potential for the treatment of type 2 diabetes mellitus," Treat Endocrine, 2002, 1(2):71-78.
Pijl et al., "Bromocriptine: a novel approach to the treatment of type 2 diabetes," *Diabetes Care.*, 23(8):1154-1161, Aug. 2000.
Ratner et al., "Cardiovascular safety of exenatide BID: an integrated analysis from controlled clinical trials in participants with type 2 diabetes," Cardiovascular Diabetology, 2011, 10:22, 10 pages.
Raymond et al., "Pharmacotherapeutic options for the treatment of depression in patients with chronic kidney disease," *Nephrol Nurs J.*, 35(3):257-263; quiz 264, May-Jun. 2008.
Reavill et al., "Metabolite involvement in bromocriptine-induced circling behaviour in rodents," *J Pharm Pharmacol.*, 32(4):278-284, Apr. 1980.
Sajki et al., "The role of anti-obesic in the treatment of metabolic syndrome," Journal of Clinical Experimental Medicine, 2005, 213(6):643-649 (with English abstract).
Santarus, Inc., Cycloset Prescribing Information, 13 pp., (2010).
Santarus, Inc., Santarus Announces Commercial Launch of of Novel Type 2 Diabetes Drug , CYCLOSET, 2 pp., (2010).
Schaper et al., "Peripheral vascular disease and Type 2 diabetes mellitus," Diabetes Metab Res Rev, 2000, 16(Suppl 1) S11-S15.
Schobel et al., "Effects of bromocriptine on cardiovascular regulation in healthy humans," *Hypertension*, 25(5):1075-1082, May 1995.
Schojaei et al., "Buccal Mucosa as a route for systemic drug delivery: A Review," J. Pharm. Pharmaceutical Science, 1998, 1(1):15-30.
Scirica et al., "Saxagliptin and cardiovascular outcomes in patients with type 2 diabetes mellitus," The New England Journal of Medicine, Oct. 3, 2013, 369(14):1317-1326.
Scranton et al., "A randomized, double-blind, placebo-controlled trial to assess safety and tolerability during treatment of type 2 diabetes with usual diabetes therapy and either CYCLOSET™ or placebo," BMC Endocrine Disorders, 2007, 7(3):1-7.
Stout, "Insulin as a mitogenic factor: role in the pathogenesis of cardiovascular disease," The American Journal of Medicine, Feb. 21, 1991, 90 (suppl 2A—62S-65S).
Suresh et al., "Intranasally delivered microdoses of bromocriptine (BCR) effectively reduced serum prolactin levels in hyperprolactinemic patients," Current Science (Bangalore), 68(5):528-531, 1995.
Takasawa, "Inhibition of dipeptidyl peptidase 4 regulates microvascular endothelial growth induced by inflammatory cytokines," Biochemical and Biophysical Research Communications, 2010, 401:7-12.
The Lipid, 2005, 16(3):265-270 (with English abstract).
Tsagarakis et al., "Effectiveness of a long-acting injectable form of bromocriptine in patients with prolactin and growth hormone secreting macroadenomas," *Clin Endocrinol (Oxf).*, 42(6):593-599,.
Turner, "Intensive blood-glucose control with sulphonylureas or insulin compared with conventional treatment and risk of complications in patients with type 2 diabetes (UKPDS 33)," UK Prospective Diabetes Study D (UKPDS) Group, The Lancet, Sep. 12, 1998, 352:837-853.
Valente et al., "Metabolite involvement in bromocriptine-induced prolactin inhibition in rats," *J Pharmacol Exp Ther.*, 282(3):1418-1424, Sep. 1997.
Vermesh et al., "Vaginal bromocriptine: pharmacology and effect on serum prolactin in normal women," *Obstetrics & Gynecology*, 72(5):693-698, 1988.
Veroscience, LLC, Prior Approval Supplement for CMC Change Utilization of Micronized Bromocriptine Mesylate (Redacted), 22 pp. (2012).
White et al., "Alogliptin after acute coronary syndrome in patients with type 2 diabetes," The New England Journal of Medicine, Oct. 3, 2013, 369(14):1327-1335.

(56) References Cited

OTHER PUBLICATIONS

Wimalasena et al., "Chiral multisubstrate inhibitors of dopamine β—monooxygenase: evidence for dual modes of interaction," American Chemical Society/Biochemistry, vol. 36, 1997, pp. 7144-7153.
Zhang et al., "Bromocriptine/skf38393 treatment ameliorates dyslipidemia in ob/ob mice," Metabolism, 1999, 48(8):1033-1040.
Zhang et al., "Inhibitory effects of bromocriptine on vascular smooth muscle cell proliferation," Atherosclerosis, 1997, 133:37-44 (Full article).
Zou et al., "Protein-protein coupling/uncoupling enables dopamine d2 receptor regulation of AMPA receptor-mediated excitotoxicity," The Journal of Neuroscience, Apr. 27, 2005, 25(17):4385-4395.
Restriction Requirement in U.S. Appl. No. 13/375,810, dated Feb. 1, 2013, 10 pages.
Non-final Office Action issued in U.S. Appl. No. 13/375,810, dated May 13, 2013, 20 pages.
Final Office Action issued in U.S. Appl. No. 13/375,810, dated Jan. 3, 2014, 9 pages.
Notice of Allowance in U.S. Appl. No. 13/375,810, dated Jul. 2, 2014, 7 pages.
Office Action in Australian Application No. 2010256366, dated Jun. 25, 2013, 4 pages.
Notice of Acceptance for Australian Application No. 2010256366, dated Aug. 7, 2014, 2 pages.
Office Action in Australian Application No. 2014265118, dated Nov. 17, 2015, 3 pages.
Office Action in CN Application No. 201080028010.6, dated Sep. 26, 2013, 16 pages (with English translation).
Rejection Decision in CN Application No. 201080028010.6, dated Jun. 13, 2014, 16 pages (with English translation).
Extended European Search Report in EP Application No. 10784223.9, dated Sep. 27, 2012, 16 pages.
Office Action in EP Application No. 10784223.9, dated Oct. 30, 2015, 6 pages.
Office Action in JP Application No. 2012-514225, dated Jun. 10, 2014, 7 pages (with English translation).
Decision of Rejection in JP Application No. 2012-514225, dated Apr. 28, 2015, 9 pages (with English tanslation).
Non Final Office Action in U.S. Appl. No. 14/506,353, dated Sep. 11, 2015, 8 pages.
Notice of Allowance in U.S. Appl. No. 14/506,353, dated Feb. 12, 2016, 7 pages.
International Search Report and Written Opinion in International Application No. PCT/US2010/037605, dated Jul. 28, 2010, 6 pages.
International Preliminary Report on Patentability in International Application No. PCT/US2010/037605, dated Dec. 6, 2011, 5 pages.
Indian Office Action in Application No. 9546/DELNP/2011, dated Jul. 24, 2017, 5 pages.
Written Submission of the Act for Pre-Grant Opposition in Application No. 9546/DELNP/2011, 23 pages.

\* cited by examiner

COMBINATION OF DOPAMINE AGONISTS PLUS FIRST PHASE INSULIN SECRETAGOGUES FOR THE TREATMENT OF METABOLIC DISORDERS

CROSS-REFERENCE TO RELATED APPLICATIONS

This application is a continuation of and claims priority to U.S. application Ser. No. 13/375,810, filed on Feb. 23, 2012, which is a 371 of International Application No. PCT/US2010/037605 filed on Jun. 7, 2010 which, in turn, claims benefit of Provisional U.S. Application Ser. No. 61/217,906 filed on Jun. 5, 2009. The contents of the prior applications are incorporated herein by reference in their entireties.

BACKGROUND OF THE INVENTION

1. Field of the Invention

The present invention is directed to agents that increase central dopaminergic activity plus first phase insulin secretagogues for the treatment of metabolic disorders.

2. Description of the Related Art

Type 2 diabetes (T2D) is characterized by both an ineffectiveness of insulin to maintain normal plasma glucose levels because of resistance of the body to its normal action to induce removal of glucose from the circulation into insulin sensitive tissues when glucose is abnormally high such as after consumption of a meal and also by beta cell failure to secrete appropriate amounts of insulin particularly following a meal/glucose challenge. This insulin resistance coupled with beta cell failure results in abnormally high circulating plasma glucose levels and is coupled with a myriad of other metabolic disorders such as dyslipidemia and hypertension that collectively predispose to cardiovascular disease, the leading cause of death in the T2D patient. Type 2 diabetes is now a global pandemic with more than 200 million people affected with the disease and the World Health Organization estimates that by 2030 there will be approximately 300 million people with the disease worldwide. Additionally, a condition termed pre-diabetes is also growing globally with approximately twice the number of affected individuals as type 2 diabetes. The definition of pre-diabetes varies among health organizations but is generally classified as Impaired Fasting Glucose (IFG) (fasting glucose levels between 110-125 mg/dl) or Impaired Glucose Tolerance (IGT) (2-hour post oral glucose load (75 g) plasma glucose greater than 140 to 199 mg per dL (7.8 to 11.0 mmol)) and is accompanied by an increased risk for the development of frank T2D. IFG and IGT are distinct metabolic abnormalities (Abdul-Ghani M A et al, Diabetes 55:1430-35, 2006). It now appears that the 1-hour post glucose load plasma glucose level is a better predictor of future T2D onset than IFG or IGT (Abdul-Ghani M A et al, Diabetes Care 32:281-86, 2009). Indeed in subjects with fasting hyperglycemia and a normal 2-hour post-glucose load plasma glucose level, it is the 1-hour plasma glucose that is most predictive of future T2D onset (Abdul-Ghani M A et al, Diabetes Care 33:557-561, 2010). Insulin secretory response to an oral glucose load is typically composed of a first-phase and second phase response. Insulin is released from the pancreas in a biphasic manner in response to a square-wave increase in arterial glucose concentration. The first phase consists of a brief spike lasting about 10 min followed by the second phase, which reaches a plateau at 2-3 h. It is widely thought that diminution of first-phase insulin release is the earliest detectable defect of β-cell function in individuals destined to develop type 2 diabetes and that this defect largely represents β-cell exhaustion after years of compensation for antecedent insulin resistance. Subjects with IGT are characterized by impaired first and second phase insulin secretory response while subjects with IFG are characterized mainly by impaired first phase insulin secretory response (Abdul-Ghani M A et al, Eur J Clin Invest in press; Ferrannini E et al, Diabetologia 46: 1211-1219, 2003). Subjects with T2D have impairments in both phases of insulin secretion. Subjects with IFG, IGT and T2D all have insulin resistance. Postprandial glucose dysmetabolism (elevated postprandial glucose levels; postprandial hyoperglycemia) has been identified as a risk factor not only for progression to T2D but also for cardiovascular disease (CVD) (Bonora E et al, Diabetologia 44:2107-14, 2001; Ceriello A et al, Nutr Metab Cardiovasc Dis 16:453-6, 2006; Di Filippo C et al, Curr Diabetes Rev 3:268-73, 2007). Therefore postprandial hyperglycemia is important to correct in the prediabetes and T2D subjects alike to improve overall metabolic and cardiovascular health. Little attention has been given to methods of treating postprandial insulin resistance however and little is known of what controls this postprandial insulin response in the muscle and liver. There are currently no methods of treatment available that improve postprandial insulin resistance and first phase insulin secretory response in subjects with prediabetes or T2D. The ability to correct both of these abnormalities would likely lead to better postprandial glucose control and health outcomes in subjects with IFG, IGT and T2D. What is needed is a simple method of treating both postprandial insulin resistance and first-phase insulin secretion as a method of improving IFG, IGT and T2D.

SUMMARY OF THE INVENTION

It has recently been determined that timed once daily administration of centrally acting dopamine agonists (such as bromocriptine) or of compounds that increase central dopaminergic activity particularly at the appropriate time of day when central/hypothalamic dopaminergic activity is high in insulin sensitive non-T2D subjects and low in such subjects, improves postprandial glucose metabolism (FDA Cycloset® package insert 2009) without increasing insulin release. This suggests that such dopamine agonist treatment may improve postprandial insulin resistance. It has now been surprisingly found that if one combines such a method of treating IFG, IGT, or T2D with a first-phase insulin secretagogue, one can produce synergistic effects to reduce these disorders. Additional dopamine agonists useful in the invention include quinpirole, quinerolane, talipexole, ropinirole, apomorphine, lisuride, terguride, fenoldopam, dihydroergotoxine, (hydergine), dihydroergocryptine, and combinations thereof. A most preferred central acting dopamine agonist is bromocriptine.

Cycloset, a quick-release, high absorbing formulation of bromocriptine mesylate, a dopamine agonist, improves glycemic control in type 2 diabetes in large part by improving postprandial responsiveness to insulin. Several drugs that directly or indirectly stimulate an increase in first phase insulin release (termed first phase insulin secretagogues) also produce improvements in glycemic control by lowering postprandial glucose levels in subjects with type 2 diabetes.

We have now found that improved glycemic control in subjects with type 2 diabetes is possible by combining these two different drug classes, e.g., agents that increase central dopamine activity plus first phase insulin secretagogues as defined herein. The combination of such dopamine activity regulating agents and first phase insulin secretagogue has been observed to have advantageous effects. First, the combination produces more than additive, i.e., synergistic, effects on glycemic control. This synergism may also be realized with dopamine agonists, such as Cycloset and short acting insulins. Secondly, the combination permits one to reduce the daily dosages of Cycloset and the insulin secretagogue and get additional benefit on glycemic control when combined at these lower dosages relative to their regular respective single dosage uses. Thirdly, the combination reduces overall side effects of each of these agents. Fourth, the metabolic benefits of improvements in lipid metabolism, blood pressure, and vascular dysfunction, and heart and kidney disease may also be realized in a similar synergistic manner with this agent increasing central dopaminergic activity—first phase insulin secretagogue drug combination. In total, this unique combination allows for synergistic increased effectiveness and simultaneous decreased side effects for treating metabolic disease at lower doses than each drug class is utilized at individually to treat such metabolic disorders.

The combination composition is effective to treat one or more metabolic disorders selected from the metabolic syndrome, Type 2 diabetes, obesity, prediabetes, key elements of any metabolic disorder, insulin resistance, hyperinsulinemia, cardiovascular disease, elevated plasma norepinephrine, elevated cardiovascular-related inflammatory factors or potentiators of vascular endothelial dysfunction, hyperlipoproteinemia, atherosclerosis, hyperphagia, hyperglycemia, hyperlipidemia, hypertension, and high blood pressure. The key elements of a metabolic disorder is selected from the group consisting of impaired fasting glucose, impaired glucose tolerance, increased waist circumference, increased visceral fat content, increased fasting plasma glucose, increased fasting plasma triglycerides, increased fasting plasma free fatty acids, decreased fasting plasma high density lipoprotein level, increased systolic or diastolic blood pressure, increased plasma postprandial triglyceride or free fatty acid levels, increased cellular oxidative stress or plasma indicators thereof, increased circulating hypercoagulative state, arteriosclerosis, coronary artery disease, peripheral vascular disease, congestive heart failure, hepatic steatosis, renal disease including renal insufficiency, and cerebrovascular disease.

First phase insulin secretagogues include but are not limited to a glucagon-like peptide-1 (GLP-1) or mimetic thereof, insulin and/or a meglitinide, repaglinide, nateglinide or a dipeptidyl peptidase inhibitor.

Multiple circadian central neural oscillations govern the regulation and coordination of multiple physiological (e.g., metabolic) events in the periphery as a function of their circadian (timing) phase relationship, described in U.S. Pat. No. 5,468,755 and herein incorporated in entirety by reference. One such circadian rhythm governing metabolic status is the central (hypothalamic) circadian rhythm of dopaminergic activity. It has previously been observed that phase shifts in the circadian rhythm of central dopaminergic activities influenced the status of obesity or diabetes. However, it has now been surprisingly found that phase shifts away from the healthy normal circadian rhythm of central or hypothalamic dopaminergic activity by environment, diet, stress, genetics and/or other factors are somehow also operative in a much different and broader physiological regulatory system and potentiate and lead to the multiple complex metabolic pathologies of and associated with metabolic syndrome as described herein. Furthermore, it has now been found that resetting these aberrant central dopaminergic circadian rhythms back towards that of the healthy normal state results in simultaneous improvements in the multiple complex pathologies of and associated with metabolic syndrome as described herein. As described above, metabolic syndrome and its associated pathologies represent a different pathology from diabetes or obesity, the cause of which is unknown. However, subjects with metabolic syndrome have much greater risk of developing cardiovascular disease than subjects without the syndrome. Inasmuch as obesity and type 2 diabetes are not always associated with metabolic syndrome and vice versa, it is clear that this major health risk represents a separate and unique metabolic state with unique characteristics. Adjusting the circadian rhythm of central dopaminergic activities by various means may be employed to reduce the many pathologies of and associated with this syndrome, for example aberrant vascular tone, vascular health, endothelial function, glucose and lipid metabolism, immune system functions specifically influencing the vasculature, insulin action, and blood coaguability. This same circadian dopaminergic resetting methodology may also be utilized to treat cardiometabolic risk, a cluster of physiological pathologies of common or discordant origin that converge to increase risk of cardiovascular disease. These risk factors include those of metabolic syndrome, but also inflammation, endothelial dysfunction, hypercholesterolemia, diabetes, obesity, smoking, gender, and age. Rather than just increasing dopaminergic activity with central dopamine agonists to improve metabolic syndrome, cardiometabolic risk and their associated pathologies, one may better influence these conditions by timing the administration of such dopamine agonists to coincide with the daily peak in central dopaminergic activities of healthy subjects of the same species to derive maximal benefit from such dopamine agonist therapy in treating these conditions.

In further accordance with this invention, the use of dopamine agonists to treat the Metabolic Syndrome (obesity, insulin resistance, hyperlipidemia, and hypertension), non-metabolic pathologies associated with MS (a pro-inflammatory state, a pro-coagulative state, pro-oxidant state, and/or endothelial dysfunction), arteriosclerosis, and/or cardiovascular disease, all in subjects with or without Type 2 diabetes, is applied during specific daily intervals to maximize the effectiveness of such treatment. Use of such centrally acting dopamine agonists for treatment of the metabolic and non-metabolic vascular disorders described herein may be potentiated by their administration at the appropriate time(s) of day. Circadian rhythms of dopaminergic activity within the central nervous system, and particularly the phase relations of these dopaminergic neuronal rhythms with other circadian neuronal activities such as serotonergic neuronal activities have been demonstrated to regulate peripheral glucose and lipid metabolism in a manner dependent upon the phase of the daily peak in circadian central dopaminergic activity. Consequently, increases in dopaminergic activity at particular times of day versus others produce maximal effectiveness in improving metabolic diseases and disorders such as type 2 diabetes, obesity, pre-diabetes, metabolic syndrome, cardiometabolic risk, hypertension, dyslipidemia, insulin resistance, hyperinsulinemia, hepatic steatosis, renal disease, cardiovascular disease, cerebrovascular disease, and peripheral vascular disease and biomarkers of impending vascular disease. As such, maximized successful treatment of these aforementioned pathologies and abnormalities may be accomplished by appropriately timed daily administration of centrally acting dopamine agonist(s). Because such dopamine agonist therapy attacks a root cause of these metabolic disorders (central dysregulation of global peripheral metabolism) it is possible to effectuate improvements in several metabolic pathologies in a simultaneous fashion that is not generally achievable by other conventional means that attack particular specific symptoms of metabolic disease for example hypertension or high cholesterol or hyperglycemia by acting at specific downstream peripheral targets such as biochemical pathways within liver or muscle. Such a treatment effect is currently lacking in the general armamentarium of therapeutics for metabolic diseases. Moreover, central dopamine agonist therapy may be coupled to direct or indirect peripheral acting therapeutic agents such as anti-diabetes agents, antihypertensive agents, cholesterol lowering agents, anti-inflammatory agents, or anti-obesity agents to produce additive improvements in metabolic disease such as obesity or type 2 diabetes or particular aspects of metabolic disease such as hypertension associated with obesity or type 2 diabetes. Details of the timing aspects of the invention can be found in copending International Patent Application Publications WO 2008/150480 and WO 2008/121258.

The novel treatment for metabolic disorders, including the metabolic syndrome (obesity, insulin resistance, hyperlipidemia, and hypertension), Type 2 diabetes, obesity, and/or prediabetes including key elements of metabolic disorders consists of administering to a mammalian species in need of such treatment a pharmaceutical composition that simultaneously stimulates an increase in central dopaminergic neuronal activity level (particularly within neurons innervating the hypothalamus and the hypothalamus itself) and a decrease in central noradrenergic neuronal activity level (particularly within the brain stem region that innervates the hypothalamus and the hypothalamus itself). It has been unexpectedly discovered that increasing the ratio of dopaminergic neuronal to noradrenergic neuronal activity within the central nervous system, particularly the hypothalamus of the central nervous system reduces metabolic disorders and improves the conditions associated with metabolic syndrome, type 2 diabetes, obesity, and/or prediabetes and key elements thereof. As defined herein, "neuronal activity" refers to either an increase or decrease in the action potential of a neuron. More specifically, as defined herein, "neuronal activity" refers to either an increase or decrease in the synaptic neurochemical signal transmission of a neuron to another thereby affecting action potential. More narrowly yet, as defined herein, "neuronal activity" refers to the biochemical communication to a (secondary [e.g., post-synaptic]) neuron from either the neurochemical signal transmission of another (primary [e.g., pre-synaptic]) neuron (e.g., as via an endogenous neurotransmitter) or from any neuromodulatory compound (e.g., an exogenous neurotransmitter receptor modulator such as a pharmaceutical agent) thereby affecting action potential or neurotransmitter release of the secondary neuron. As such, an increase in dopaminergic neuronal activity would be characterized by a) an increase in release of dopamine molecules from a dopamine producing (primary) neuron, an increase in dopamine molecules within the synapse by any mechanism, and/or increase in dopamine-mimetic compound(s) from any source (e.g., pharmaceutical) resulting in increased binding to dopaminergic receptor sites of other (secondary) neuron (s) that affect said other neuron(s)' action potential or neurotransmitter release in a manner consistent with increased dopamine ligand-dopamine receptor binding signal transduction (e.g., post-synaptic dopamine receptor agonist) and/or b) an increase in sensitivity or responsiveness of said "other (secondary)" neuron(s) to such dopamine or dopamine-mimetic compound(s)' ability to affect action potential or neurotransmitter release in said "other (secondary)" neuron (e.g., as an increase in dopamine receptor number or affinity or responsiveness). Contrariwise, dopamine-mimetic binding to dopamine-producing neurons (i.e., presynaptic dopamine neurons) and/or increased sensitivity or responsiveness of dopamine producing neurons to respond to neurotransmitters or neuromodulators that thereby reduces dopamine release would be considered an activity leading to a decrease in dopaminergic neuronal activity [and, when considered in and of itself, is an undesirable aspect of dopaminergic activity respecting this invention]. For the sake of clarity, post-synaptic dopamine receptor agonists include dopamine D1, D2, D3, D4, and D5 receptor agonists and post-synaptic norepinephrine receptor antagonists include alpha 2bc and alpha1 antagonists.

DETAILED DESCRIPTION OF THE INVENTION

Materials and Methods
Animal Studies
Male Syrian hamsters known to develop insulin resistance and glucose intolerance were purchased at 4 weeks of age and kept on rodent diet for 10 weeks at 72 degrees F. and a 14 hr:10 hr daily light:dark cycle. When animals were 14 weeks of age on this daily photoperiod (known to be insulin resistant and glucose intolerant under these conditions), bromocriptine mesylate was administered intraperitoneally (IP) for 2 weeks at 4 mg/kg per hamster 13 hours after light onset to half of the animals, while the other half received vehicle injections for 2 weeks.

After 2 weeks of treatment both Bromocriptine and vehicle groups were divided into two groups for a total of 4 groups: 1. Vehicle for 2 weeks and Vehicle at initiation of a glucose tolerance test (GTT); 2. Vehicle for 2 weeks and Exendin-4 at initiation of the GTT; 3. Bromocriptine for 2 weeks and Vehicle at GTT; 4. Bromocriptine for 2 weeks and Exendin-4 at GTT.

Glucose tolerance test was performed among all 4 study groups on Day 15 of the study by challenge with 3 g/kg body weight of glucose at 7 hours after light onset among each of the 4 treatment groups—(bromocriptine or vehicle treatment for 2 weeks and with IP injection of either vehicle or 4 µg/kg of Exendin-4, a GLP-1 analog [Sigma Chemical, St Louis, Mo.] dissolved in saline) at the GTT. Also, an additional group of hamsters treated with vehicle for 2 weeks received Exendin-4 on the day of GTT at 8 µg/kg. Blood was drawn from the jugular vein and blood glucose level was measured every 30 minutes for 2 hours after the glucose load administration.

In a similarly designed experiment among 4 groups of animals, insulin was injected IP at 240 ng/kg in place of Exendin-4 as the first phase insulin secretagogue (FPIS).

Human Studies
494 obese Type 2 diabetes subjects who were poorly controlled on a sulphonylurea dose that was stable for at least 60 days prior to study initiation were enrolled in a multicentre study, with 244 randomized to treatment with Cycloset plus a stabilized dose of currently used sulphonylurea, and 250 randomized to treatment with placebo plus a stabilized dose of currently used sulphonylurea. Subjects were admitted to a clinical research center one week prior and 24 weeks after the start of Cycloset administration and administered standardized meals at breakfast lunch and dinner. One-hour postprandial plasma insulin and glycated hemoglobin A1c (HbA1c) (a measure of glycemic control) were measured one week prior and 24 weeks after the start of Cycloset administration. Cycloset induced improvements in HbA1c relative to placebo were analyzed as a function of the baseline 1-hour postprandial insulin level in the study subjects.

Results

Animal Studies

Timed Bromocriptine administration for 2 weeks did not statistically significantly reduced blood glucose Area Under Curve (AUC) during the GTT over two hours after glucose administration (21% reduction, P<0.09). Likewise Exendin-4 immediately prior to glucose administration at either 4 ug/kg or 8 ug/kg did not statistically significantly reduced blood glucose Area Under Curve (AUC) during the GTT over two hours after glucose administration (19% and 27% reduction, P=0.23 and P=0.13 respectively). However, in animals that were treated both with bromocriptine for 2 weeks and received Exendin-4 at 4 ug/kg prior to GTT initiation a statistically significant decrease of Glucose AUC of 60% was observed (P<0.0002). Thus no statistically significant effect of either the dopamine agonist treatment or of the first-phase insulin secretagogue on glucose intolerance was observed, yet the combination of the two produced a marked improvement in glucose intolerance, the numerical value of which was 50% greater than the addition of the two drug effects separately and also more than double the effect of doubling the dose of exendin-4 (P=0.05). Even when viewed in these terms, a 50% reduction in the GTT AUC represents a robust improvement in relative glucose intolerance (Ceriello A et al Nutr Metab Cardiovasc Dis 16:453-6, 2006; Abdul-Ghani M A et al, Diabetes Care 32: 281-86, 2009). This synergistic effect of these agents (0+0=marked effect) allows for the lowering of the first-phase insulin secretagogue (FPIS) dose and yet to achieve better results when combined with a centrally acting dopamine agonist (as evidenced by the result that 2× the Exendin-4 dose did not produce any benefit to glucose intolerance and was not even half the numerical effect of the dopamine agonist/half FPIS dose on glucose intolerance). The lowering of the FPIS allows for reducing its side effects and strain on the beta cell (beta cell exhaustion) which is beneficial to the treated subject.

In a similarly designed experiment as above but replacing the FPIS from exendin-4 to exogenous insulin itself, glucose AUC over two hours after such glucose administration was not significantly reduced by 2 weeks of treatment with bromocriptine (28% reduction, P=0.23) or by insulin administration immediately prior to glucose administration (P=0.64). However, animals that were both treated with Bromocriptine for 2 weeks and received insulin prior to the GTT exhibited a decrease of Glucose AUC of 55% (P=0.014). Once again, the combination of a FPIS (insulin) plus a central acting dopamine agonist produces an effect much greater than the sum of the individual treatments as each were ineffective in producing any beneficial result. Once again, even when viewed in numerical terms irrespective of statistical significance, the combination produced a reduction in glucose intolerance of 50% greater than the addition of each therapy alone which as stated above is a marked improvement in glucose intolerance with demonstrable health benefits.

The observation that this synergism is achieved with 2 markedly different FPIS molecules that share only the ability to increase plasma insulin level after a meal when administered prior to the meal indicates that this is a class phenomenon and not something particular to the FPIS agents employed. Previously it has been demonstrated that various agents that increase central dopaminergic activity all improve metabolic disorders, again indicating that the phenomenon, in a general sense, is not molecule specific, but rather a class effect. Therefore, this synergism may be fully expected to be a class interaction synergism.

Inasmuch as meals for humans are typically 3 times per day, it is possible to reduce this combination synergistic therapeutic for metabolic disorders to a once-daily dosing by preparing long acting FPIS with short acting agents that increase central dopaminergic activity at specific time of day only in unique dosage forms. Such dosage forms provide the benefit of the synergism, allow for the maximal effect of the dopamine stimulation by timing it to the appropriate time of day, and provide for convenience of use (only a single administration per day). Such dosage forms may take the form of non-oral or oral routes of administration.

Human Studies

The average 1-hour postprandial plasma insulin level was 50 µU/ml in both Cycloset and Placebo treated groups at the start of the study; incoming HbA1C was 9.4% and 9.5% respectively. In the Cycloset treated group HbA1C was reduced by 0.3% over 24 weeks of treatment, while HbA1C went up by 0.26% in the Placebo arm (P<0.0001). For subjects with incoming 1-hour postprandial insulin <30 uU/ml there was no effect of Cycloset on HbA1c, for subjects with incoming 1-hour postprandial >30 uU/ml and <50 uU/ml the Cycloset effect was −0.57 (P<0004) and among subjects with incoming 1-hour postprandial insulin >50 µU/ml the Cycloset effect on HbA1C was −0.79 (P<0.0001).

These results indicate that the effect of the dopamine agonist to improve glycemic control in T2D subjects is positively correlated with 1-hour postprandial insulin level in the subjects supporting the concept that the combination of an agent that increases central dopaminergic activity with a FPIS will produce synergistic improvements in glucose metabolism. Moreover the collective results of these animal and human studies indicate that pharmaceutical agents that preserve pancreatic beta cell function per se, i.e., retard the loss of appropriate beta cell insulin responsiveness to meal glucose (and as such improve postprandial insulin secretory response to glucose) such as thiazolidinediones and glucagon like peptide 1 analogs, will also synergize with agents that increase central dopaminergic activity to improve metabolic disorders and produce long lasting benefit on glycemic control (e.g., for a year or more). This combination of therapies for the treatment of metabolic disorders is also envisioned by this invention as well.

Exendin-4

Exendin-4, a 39 amino acid peptide, originally isolated from *Heloderma suspectum* (Gila monster lizard) venom, activates GLP-1 (glucagon-like peptide-1) receptors to increase intracellular cAMP in pancreatic acinar cells. Synthetic Exendin-4 is also known as Exenatide, or Byetta; its molecular weight is: 4187.

GLP-1 is a gastrointestinal hormone, which regulates blood glucose primarily by stimulating glucose-dependent insulin release (first phase insulin secretion). Exendin-4 is a high affinity glucagon-like peptide 1 (GLP-1) receptor agonist (Kd=136 pM). Exendin-4 is a long-acting agonist of the GLP-1 receptor. Exenatide has comparable potency to GLP-1 and is resistant to degradation by DPP-IV. Exenatide improves glycemic control primarily by reducing postprandial hyperglycemia.

Exendin-4 dose used in this study is comparable to the dose used in the studies reported by Strauss et al., 2008 and Nachnani et al., 2010.

REFERENCES

Cervera et al., (2008) Mechanism of action of exenatide to reduce postprandial hyperglycemia in type 2 diabetes. Am J Physiol Endocrinol Metab 294: E846-E852.

Eng, J. et al., (1992) Isolation and characterization of exendin-4 an exendin-3 analogue from Heloderma suspectum venom. J. Biol. Chem. 267, 7402.

Goke et al (1993) Exendin-4 is a high potency agonist and truncated exendin-(9-39)-amide an antagonist at the glucagon-like peptide 1-(7-36)-amide receptor of insulin-secreting b-cells. J. Biol. Chem. 268 19650.

Nachnani J. et al., (2010) Biochemical and histological effects of exendin-4 (exenatide) on the rat pancreas. Diabetologia 53:153-159.

Thorens et al (1993) Cloning and functional expression of the human islet GLP-1 receptor. Diabetes 42 1678.

Strauss A. et al., (2008) Exendin-4 improves the oral glucose tolerance in diabetic rats: pancreas regeneration, better function of pancreatic islets, or impaired glucose uptake? Transplantation Proceedings, 40, 533-535

What is claimed is:

1. A method of treating a metabolic disorder or key elements of a metabolic disorder such method comprising the step of administering to a subject having a metabolic disorder or a patient in need thereof, (a) a dopamine receptor agonist; and (b) a first-phase insulin secretagogue selected from the group consisting of glucagon like peptide-1 (GLP-1) or an analog thereof, a dipeptidyl peptidase inhibitor, gastric inhibitory polypeptide (also known as glucose-dependent insulinotropic peptide), a meglitinide, repaglinide, nateglinide, postprandial insulin, a thiazolidinedione and short acting insulin, wherein the dosage of each of said dopamine receptor agonist and first-phase insulin secretagogue in combination, provides a therapeutic effect greater than the additive effect of administering the same dosage of each of said dopamine receptor agonist and first-phase insulin secretagogue alone, and wherein the dopamine receptor agonist and the first-phase insulin secretagogue are administered at the same time.

2. The method of claim 1, wherein said dopamine receptor agonist and the first-phase insulin secretagogue are administered within 4 hours of waking in the morning.

3. The method of claim 1, wherein said dopamine receptor agonist is a dopamine D2 receptor agonist selected from the group consisting of bromocriptine, lisuride, hydergine, dihydroergotoxine, and other dopamine D2 receptor agonists with low or no serotonin 2B receptor agonist activity.

4. The method of claim 1, wherein the metabolic disorder is selected from the group consisting of pre-diabetes, Impaired Fasting Glucose, Impaired Glucose Tolerance and Type 2 diabetes.

5. The method of claim 1, wherein the metabolic disorder is selected from the group consisting of metabolic syndrome, Type 2 diabetes, obesity, prediabetes, insulin resistance, hyperinsulinemia, cardiovascular disease, elevated plasma norepinephrine, elevated cardiovascular-related inflammatory factors or potentiators of vascular endothelial dysfunction, hyperlipoproteinemia, atherosclerosis, hyperphagia, hyperglycemia, hyperlipidemia, hypertension, and high blood pressure.

6. The method of claim 1, wherein the key elements of metabolic disorders are selected from the group consisting of impaired fasting glucose, impaired glucose tolerance, increased waist circumference, increased visceral fat content, increased fasting plasma glucose, increased fasting plasma triglycerides, increased fasting plasma free fatty acids, decreased fasting plasma high density lipoprotein level, increased systolic or diastolic blood pressure, increased plasma postprandial triglyceride or free fatty acid levels, increased cellular oxidative stress or plasma indicators thereof, increased circulating hypercoagulative state, arteriosclerosis, coronary artery disease, peripheral vascular disease, congestive heart failure, hepatic steatosis, renal disease including renal insufficiency, and cerebrovascular disease.

7. The method of claim 1, wherein the metabolic disorder is selected from the group consisting of glucose intolerance or insulin resistance.

8. The method of claim 1, wherein the metabolic disorder is Type 2 diabetes or pre-diabetes.

9. The method of claim 1, wherein the dosage of the dopamine receptor agonist is insufficient to effectively treat said disorder or key elements of said disorder without co-administration of the first-phase insulin secretagogue.

10. The method of claim 1, wherein the dosage of the first-phase insulin secretagogue is insufficient to effectively treat the disorder or key elements of the disorder without co-administration of the dopamine receptor agonist.

11. The method of claim 1, wherein the dosage of each of the dopamine receptor agonist and the first-phase insulin secretagogue in combination are effective to treat the disorder or key elements of the disorder.

12. The method of claim 1, wherein the dopamine receptor agonist is selected from the group consisting of quinpirole, quinelorane, talipexole, ropinirole, apomorphine, terguride, fenoldopam, dihydroergocryptine and combinations thereof.

13. The method of claim 1, wherein the dosage of said first-phase insulin secretagogue effective to treat said disorder when administered with said dopamine receptor agonist is less than the dosage of said secretagogue effective to treat said disorder when administered without said dopamine receptor agonist.

14. The method of claim 1, wherein the dopamine receptor agonist is a combination of a dopamine D1 receptor agonist and a dopamine D2 receptor agonist.

15. The method of claim 1, wherein the dopamine receptor agonist is bromocriptine or a pharmaceutically acceptable salt thereof.

16. The method of claim 15, wherein the dopamine receptor agonist is bromocriptine mesylate.

17. The method of claim 1, wherein the subject is a mammal.

18. The method of claim 17, wherein the mammal is a human.

19. The method of claim 1, wherein the dopamine receptor agonist and the first phase insulin secretagogue are administered at the same time.

20. The method of claim 1, wherein the dopamine receptor agonist and the first phase insulin secretagogue are administered together in a single dosage form.

21. The method of claim 1, wherein the dopamine receptor agonist and the first phase insulin secretagogue are administered together in a single dosage form.

22. A method of treating glucose intolerance or insulin resistance in a mammal in need of such treatment, such method comprising: administering to a mammal suffering from glucose intolerance or insulin resistance (a) bromocriptine or a pharmaceutically acceptable salt thereof; and (b) a first-phase insulin secretagogue selected from the group consisting of GLP-1 or an analog thereof and insulin, wherein the dosage of each of bromocriptine or a pharmaceutically acceptable salt thereof and first-phase insulin secretagogue in combination, provides a therapeutic effect greater than the additive effect of administering the same dosage of each of said bromocriptine or a pharmaceutically acceptable salt thereof and said first-phase insulin secretagogue alone and wherein the bromocriptine or a pharmaceutically acceptable salt thereof and the first-phase insulin secretagogue are administered at the same time.

23. The method of claim 22, wherein said bromocriptine or a pharmaceutically acceptable salt thereof and the first-phase insulin secretagogue are administered to a human to increase central dopaminergic activity within 4 hours of waking in the morning.

24. The method of claim 22, wherein the salt is mesylate.

25. The method of claim 22, wherein the mammal is suffering from type 2 diabetes.

26. A method of treating a metabolic disorder or key elements of a metabolic disorder such method comprising the step of administering to a patient having a metabolic disorder or a patient in need thereof, (a) a dopamine receptor agonist; and (b) a first-phase insulin secretagogue selected from the group consisting of glucagon like peptide-1 (GLP-1) or an analog thereof, a dipeptidyl peptidase inhibitor, gastric inhibitory polypeptide (also known as glucose-dependent insulinotropic peptide), a meglitinide, repaglinide, nataglinide, postprandial insulin, a thiazolidinedione and short acting insulin, wherein the dosage of each of said dopamine receptor agonist and first-phase insulin secretagogue in combination, provides a therapeutic effect greater than the additive effect of administering the same dosage of each of said dopamine receptor agonist and first-phase insulin secretagogue alone and wherein the dopamine receptor agonist and first phase insulin secretagogue are administered at the same time.

27. The method of claim 26, wherein the dopamine receptor agonist is selected from the group consisting of bromocriptine, lisuride, hydergene, dihydroergotoxine, and other dopamine D2 receptor agonists with low or no serotonin 2B receptor agonist activity.

28. The method of claim 26, wherein metabolic disorder is selected from the group consisting of pre-diabetes, Impaired Fasting Glucose, Impaired Glucose Tolerance and Type 2 diabetes.

29. The method of claim 26, wherein the metabolic disorder is selected from the group consisting of the metabolic syndrome, Type 2 diabetes, obesity, prediabetes, insulin resistance, hyperinsulinemia, cardiovascular disease, elevated plasma norepinephrine, elevated cardiovascular-related inflammatory factors or potentiators of vascular endothelial dysfunction, hyperlipoproteinemia, atherosclerosis, hyperphagia, hyperglycemia, hyperlipidemia, hypertension, and high blood pressure.

30. The method of claim 26, wherein the key elements of metabolic disorders are selected from the group consisting of impaired fasting glucose, impaired glucose tolerance, increased waist circumference, increased visceral fat content, increased fasting plasma glucose, increased fasting plasma triglycerides, increased fasting plasma free fatty acids, decreased fasting plasma high density lipoprotein level, increased systolic or diastolic blood pressure, increased plasma postprandial triglyceride or free fatty acid levels, increased cellular oxidative stress or plasma indicators thereof, increased circulating hypercoagulative state, arteriosclerosis, coronary artery disease, peripheral vascular disease, congestive heart failure, hepatic steatosis, renal disease including renal insufficiency, and cerebrovascular disease.

31. The method of claim 26, wherein said dopamine receptor agonist and first-phase insulin secretagogue are administered to a patient to increase central dopaminergic activity within 4 hours of waking in the morning.

32. The method of claim 26, wherein the dosage of the dopamine receptor agonist is insufficient to effectively treat said disorder or key elements of said disorder without co-administration of the first-phase insulin secretagogue.

33. The method of claim 26, wherein the dosage of the first-phase insulin secretagogue is insufficient to effectively treat said disorder or key elements of said disorder without co-administration of the dopamine receptor agonist.

34. The method of claim 26, wherein the dosage of each of the dopamine receptor agonist and the first-phase insulin secretagogue in combination are effective to treat said disorder or key elements of said disorder.

35. The method of claim 26, wherein the dopamine receptor agonist is selected from the group consisting of quinpirole, quinerolane, talipexole, ropinirole, apomorphine, terguride, fenoldopam, dihydroergocryptine and combinations thereof.

36. The method of claim 26, wherein the dosage of said first-phase insulin secretagogue effective to treat said disorder when administered with said dopamine receptor agonist is less than the dosage of said secretagogue effective to treat said disorder when administered without said dopamine receptor agonist.

37. The method of claim 26, wherein the dopamine receptor agonist is a combination of a dopamine D1 receptor agonist and a dopamine D2 receptor agonist.

38. The method of claim 26, wherein the dopamine receptor agonist is bromocriptine or a pharmaceutically acceptable salt thereof.

39. The method of claim 38, wherein the dopamine receptor agonist is bromocriptine mesylate.

40. The method of claim 26, wherein the dopamine receptor agonist and the first phase insulin secretagogue are administered at the same time.

41. The method of claim 26, wherein the dopamine receptor agonist and the first phase insulin secretagogue are administered together in a single dosage form.

42. A method of treating glucose intolerance or insulin resistance in a mammal in need of such treatment, such method comprising: administering to a mammal suffering from glucose intolerance or insulin resistance (a) a dopamine D2 receptor agonist selected from the group consisting of bromocriptine, lisuride, hydergene, dihydroergotoxine, and other dopamine D2 receptor agonists with low or no serotonin 2B receptor agonist activity; and (b) a first-phase insulin secretagogue selected from the group consisting of glucagon like peptide-1 (GLP-1) or an analog thereof, a dipeptidyl peptidase inhibitor, gastric inhibitory polypeptide (also known as glucose-dependent insulinotropic peptide), a meglitinide, repaglinide, nataglinide, postprandial insulin, a thiazolidinedione and short acting insulin, wherein the dosage of each of said dopamine D2 receptor agonist and first-phase insulin secretagogue in combination provides a therapeutic effect greater than the additive effect of administering the same dosage of each of said dopamine D2 receptor agonist and first-phase insulin secretagogue alone and wherein the dopamine receptor agonist and first phase insulin secretagogue are administered at the same time.

43. The method of claim 42, wherein said dopamine receptor agonist and first phase insulin secretagogue are administered to a human to increase central dopaminergic activity within 4 hours of waking in the morning.

44. A method of treating a metabolic disorder or key elements of a metabolic disorder such method comprising the step of administering to a patient having a metabolic disorder or a patient in need thereof, (a) a dopamine receptor agonist; and (b) a first-phase insulin secretagogue selected from the group consisting of glucagon like peptide-1 (GLP-1) or an analog thereof, a dipeptidyl peptidase inhibitor, gastric inhibitory polypeptide (also known as glucose-dependent insulinotropic peptide), a meglitinide, repaglinide, nataglinide, postprandial insulin, a thiazolidinedione and short acting insulin, wherein the dosage of each of said dopamine receptor agonist and first-phase insulin in combination, provides a therapeutic effect greater than the additive effect of administering the same dosage of each of said dopamine receptor agonist and first-phase insulin secretagogue alone and wherein said dopamine receptor agonist and said first phase insulin secretagogue are administered at the same time.

45. The method of claim 44, wherein the dopamine receptor agonist is selected from the group consisting of bromocriptine, lisuride, hydergene, dihydroergotoxine, and other dopamine D2 receptor agonists with low or no serotonin 2B receptor agonist activity.

46. The method of claim 44, wherein the metabolic disorder is selected from the group consisting of pre-diabetes, Impaired Fasting Glucose, Impaired Glucose Tolerance and Type 2 diabetes.

47. The method of claim 44, wherein the metabolic disorder is selected from the group consisting of the metabolic syndrome, Type 2 diabetes, obesity, prediabetes, insulin resistance, hyperinsulinemia, cardiovascular disease, elevated plasma norepinephrine, elevated cardiovascular-related inflammatory factors or potentiators of vascular endothelial dysfunction, hyperlipoproteinemia, atherosclerosis, hyperphagia, hyperglycemia, hyperlipidemia, hypertension, and high blood pressure.

48. The method of claim 44, wherein the key elements of metabolic disorders are selected from the group consisting of impaired fasting glucose, impaired glucose tolerance, increased waist circumference, increased visceral fat content, increased fasting plasma glucose, increased fasting plasma triglycerides, increased fasting plasma free fatty acids, decreased fasting plasma high density lipoprotein level, increased systolic or diastolic blood pressure, increased plasma postprandial triglyceride or free fatty acid levels, increased cellular oxidative stress or plasma indicators thereof, increased circulating hypercoagulative state, arteriosclerosis, coronary artery disease, peripheral vascular disease, congestive heart failure, hepatic steatosis, renal disease including renal insufficiency, and cerebrovascular disease.

49. The method of claim 44, wherein said dopamine receptor agonist is administered to a patient to increase central dopaminergic activity within 4 hours of waking in the morning.

50. The method of claim 44, wherein the dosage of the dopamine receptor agonist is insufficient to effectively treat said disorder or key elements of said disorder without co-administration of the first-phase insulin secretagogue.

51. The method of claim 44, wherein the dosage of the first-phase insulin secretagogue is insufficient to effectively treat said disorder or key elements of said disorder without co-administration of the dopamine receptor agonist.

52. The method of claim 44, wherein the dosage of each of the dopamine receptor agonist and the first-phase insulin secretagogue in combination are effective to treat said disorder or key elements of said disorder.

53. The method of claim 44, wherein the dopamine receptor agonist is selected from the group consisting of quinpirole, quinerolane, talipexole, ropinirole, apomorphine, terguride, fenoldopam, dihydroergocryptine and combinations thereof.

54. The method of claim 44, wherein the dosage of said first-phase insulin secretagogue effective to treat said disorder when administered with said dopamine receptor agonist is less than the dosage of said secretagogue effective to treat said disorder when administered without said dopamine receptor agonist.

55. The method of claim 44, wherein the dopamine receptor agonist is a combination of a dopamine D1 receptor agonist and a dopamine D2 receptor agonist.

56. The method of claim 44, wherein the dopamine receptor agonist is bromocriptine or a pharmaceutically acceptable salt thereof.

57. The method of claim 44, wherein the dopamine receptor agonist is bromocriptine mesylate.

* * * * *